United States Patent
Jeannin

(12)
(10) Patent No.: US 6,685,954 B2
(45) Date of Patent: Feb. 3, 2004

(54) INSECTICIDAL COMBINATION TO CONTROL MAMMAL FLEAS, IN PARTICULAR FLEAS ON CATS AND DOGS

(75) Inventor: Philippe Jeannin, Tournefeuille (FR)

(73) Assignee: Merial, Lyons (FR)

( * ) Notice: Subject to any disclaimer, the term of this patent is extended or adjusted under 35 U.S.C. 154(b) by 0 days.

(21) Appl. No.: 10/052,597

(22) Filed: Jan. 17, 2002

(65) Prior Publication Data

US 2002/0090387 A1 Jul. 11, 2002

Related U.S. Application Data

(63) Continuation of application No. 09/619,082, filed on Jul. 17, 2003, which is a division of application No. 08/863,692, filed on May 27, 1997, now Pat. No. 6,096,329, which is a continuation-in-part of application No. 08/692,113, filed on Aug. 5, 1996, now abandoned.

(30) Foreign Application Priority Data

Mar. 29, 1996 (FR) .............................................. 96 04208
Mar. 26, 1997 (FR) .............................................. 97 03711

(51) Int. Cl.$^7$ .......................... A01N 43/56; A01N 43/40
(52) U.S. Cl. ........................ 424/405; 514/407; 514/875; 514/341
(58) Field of Search .......................... 424/405; 514/407, 514/341, 875

(56) References Cited

U.S. PATENT DOCUMENTS

| | | | |
|---|---|---|---|
| 4,973,589 A | 11/1990 | Barnett et al. | 514/245 |
| 5,439,924 A | 8/1995 | Miller | 514/345 |
| 5,516,787 A | 5/1996 | Takada | 514/407 |
| 5,567,429 A | 10/1996 | Senbo | 424/405 |
| 5,612,047 A | 3/1997 | Duffy et al. | 424/405 |
| 5,629,334 A | 5/1997 | Takada | 514/407 |
| 6,221,894 B1 * | 4/2001 | Meinke et al. | 514/410 |

FOREIGN PATENT DOCUMENTS

| | | | |
|---|---|---|---|
| EP | 0 295 117 A1 | 12/1988 | |
| WO | 95/33380 | 12/1995 | .......... A01N/47/34 |
| WO | WO 98/25466 | 6/1998 | |

OTHER PUBLICATIONS

Postal et al, "Field Efficiency of a Mechanical Pump Spray Formulation Containing 0.25% Fipronil in the Treatment and Control of Flea Infestation and Associated Dermatological Signs in Dogs and Cats", Veterinary Dermatology. 6(3):153–158.

* cited by examiner

*Primary Examiner*—S. Mark Clardy
(74) *Attorney, Agent, or Firm*—Frommer, Lawrence & Haug, LLP; William S. Frommer; Thomas J. Kowalski

(57) ABSTRACT

Process and composition, in particular for controlling fleas on small mammals, characterized in that the composition includes, on the one hand, at least one insecticide of 1-N-arylpyrazole type, in particular fipronil, and, on the other hand, at least one compound of IGR (insect growth regulator) type, in doses and proportions which are parasiticidally effective on fleas, in a fluid vehicle which is acceptable for the animal and convenient for local application to the skin, preferably localized over a small surface area.

36 Claims, No Drawings

INSECTICIDAL COMBINATION TO CONTROL MAMMAL FLEAS, IN PARTICULAR FLEAS ON CATS AND DOGS

RELATED APPLICATIONS

This application is a continuation of U.S. Ser. No. 09/619,082, filed Jul. 17, 2000, abandoned, which in turn is a divisional of application U.S. Ser. No. 08/863,692, filed on May 27, 1997, now U.S. Pat. No. 6,096,329, which in turn is a continuation-in-part of application U.S. Ser. No. 08/692,113, filed on Aug. 5, 1996, now abandoned which in turn claims priority to French application 96 04 208, filed Mar. 29, 1996 and to French application 97 03 711, filed Mar. 26, 1997, all herein incorporated by reference.

The present invention relates to an improvement to the processes for controlling mammal fleas and in particular fleas on cats and dogs. The invention also relates to a novel composition for this use, based on a synergistic combination of parasiticides which are already known. Lastly, the invention relates to the use of such already-known parasiticides for the preparation of such a composition.

A novel class of 1-N-arylpyrazole-based 1(insecticides has been described in patents EP-A-295,217 and EP-A-352,944. The compounds of the classes defined in these patents are highly active, and one of these compounds 1-[2,6-$Cl_2$ 4-$CF_3$ phenyl]3-CN 4-[SO—$CF_3$]5-$NH_2$ pyrazole, whose common name is fipronil, has proven to be particularly effective not only against crop parasites but also against mammal ectoparasites and in particular, but not exclusively, fleas, ticks, flies and myiases.

Compounds with an ovicidal and/or larvicidal effect on the immature stages of various ectoparasites are already known, for example from patent U.S. Pat. No. 5,439,924. Among these compounds are featured insect growth regulator compounds (IGR) which act either by blocking the development of the immature stages (eggs and larvae) into adult stages, or by inhibiting the synthesis of chitin.

Patent FR-A-2,713,889 is moreover known, which generally describes the combination of at least one compound of IGR (insect growth regulator) type, comprising compounds with juvenile hormone activity and chitin synthesis inhibitors, with at least one of three N-aryldiazole compounds, in particular fipronil, to control many harmful insects belonging to very varied orders.

The compositions may be used in very diverse forms, although the applications, for example veterinary, healthcare or plant-protection applications, for which these different forms are designed are not specified, nor are the parasites for which they are respectively intended.

The only application which may be thought to be veterinary is associated with the example of the manufacture of a pesticidal collar which is a slow-release formulation.

The invention proposes to improve the processes for controlling fleas in small mammals, and in particular in cats and dogs.

The object of the invention is, in particular, to use already-known parasiticides in order to prepare a composition which is highly active against the fleas of these animals.

Lastly, the object of the invention is a novel composition thus prepared and intended, in particular, to control fleas.

For the purposes of the present invention, the term flea is understood to refer to all the usual or accidental species of parasitic flea of the order Siphonaptera, and in particular the species Ctenocephalides, in particular *C. felis* and *C. canis*, rat fleas (*Xenopsylla cheopis*) and human fleas (*Pulex irritans*).

The very high efficacy of the process and of the composition according to the invention implies not only high immediate efficacy but also very long-lasting efficacy after the animal has been treated.

The subject of the invention is a process for controlling the fleas of small mammals, and in particular cats and dogs, over a long period, characterized in that the animal is treated by locally depositing on the skin, preferably localized over a small surface area (spot-on application), in parasiticidally effective doses and proportions, on the one hand at least one compound (A) belonging to formula (I),

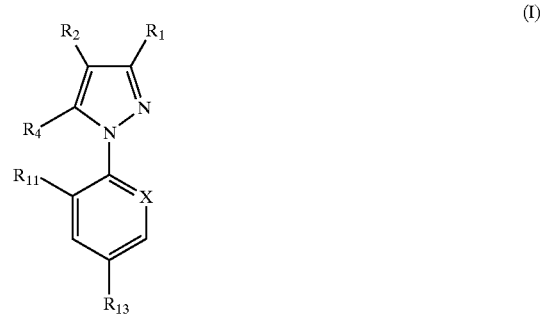

(I)

in which:
- $R_1$ is CN or methyl or a halogen atom;
- $R_2$ is $S(O)_n R_3$ or 4,5-dicyanoimidazol-2-yl or haloalkyl;
- $R_3$ is alkyl or haloalkyl;
- $R_4$ represents a hydrogen or halogen atom; or a member of a group consisting of $NR_5 R_6$, $S(O)_m R_7$, $C(O)R_7$, $C(O)O$—$R_7$, alkyl, haloalkyl, $OR_8$ and —N=$C(R_9)$ ($R_{10}$);
- $R_5$ and $R_6$ independently represent a hydrogen atom or an alkyl, haloalkyl, C(O)alkyl, alkoxycarbonyl or $S(O)_r$—$CF_3$ radical; or $R_5$ and $R_6$ may together form a divalent alkylene radical which may be interrupted by one or two divalent hetero atoms such as oxygen or sulphur;
- $R_7$ represents an alkyl or haloalkyl radical;
- $R_8$ represents an alkyl or haloalkyl radical or a hydrogen atom;
- $R_9$ represents an alkyl radical or a hydrogen atom;
- $R_{10}$ represents a phenyl or heteroaryl group optionally substituted with one or more halogen atoms or a member of the group consisting of OH, —O-alkyl, S-alkyl, cyano and alkyl;
- $R_{11}$ and $R_{12}$ represent, independently of each other, a hydrogen or halogen atom, or possibly CN or $NO_2$;
- $R_{13}$ represents a halogen atom or a haloalkyl, haloalkoxy, $S(O)_q CF_3$ or $SF_5$ group;
- m, n, q and r represent, independently of each other, an integer equal to 0, 1 or 2
- X represents a trivalent nitrogen atom or a radical C—$R_{12}$, the other three valency positions of the carbon atom forming part of the aromatic ring with the proviso that when $R_1$ is methyl, either $R_3$ is haloalkyl, $R_4$ is $NH_2$, $R_{11}$ is Cl, $R_{13}$ is $CF_3$ and X is N; or $R_2$ is 4,5-dicyanoimidazol-2-yl, $R_4$ is Cl, $R_{11}$ is Cl, $R_{13}$ is $CF_3$ and X is =C—Cl;

and, on the other hand at least one compound (B), of IGR (insect growth regulator) type, in a fluid 10 vehicle which is acceptable for the animal and suitable for local application on the skin.

Preferably, one uses at least one compound (A) belonging to the formula (I) in which:

$R_1$ is CN or methyl $R_2$ is $S(O)_nR_3$ $R_3$ is alkyl or haloalkyl $R_4$ represents a hydrogen or halogen atom; or a radical $NR_5R_6$, $S(O)_mR_7$, $C(O)R_7$, alkyl, haloalkyl or $OR_8$ or a radical —N=C($R_9$) ($R_{10}$)

$R_5$ and $R_6$ independently represent a hydrogen atom or an alkyl, haloalkyl, C(O)alkyl or $S(O)_r$—$CF_3$ radical; or $R_5$ and $R_6$ may together form a divalent alkylene radical which may be interrupted by one or two divalent hetero atoms such as oxygen or sulphur $R_7$ represents an alkyl or haloalkyl radical $R_8$ represents an alkyl or haloalkyl radical or a hydrogen atom $R_9$ represents an alkyl radical or a hydrogen atom $R_{10}$ represents a phenyl or heteroaryl group optionally substituted with one or more halogen atoms or groups such as OH, —O-alkyl, S-alkyl, cyano or alkyl $R_{11}$ and $R_{12}$ represent, independently of each other, a hydrogen or halogen atom $R_{13}$ represents a halogen atom or a haloalkyl, haloalkoxy, $S(O)_qCF_3$ or $SF_5$ group m, n, q and r represent, independently of each other, an integer equal to 0, 1 or 2

X represents a trivalent nitrogen atom or a radical C—$R_{12}$, the other three valency positions of the carbon atom forming part of the aromatic ring with the proviso that when $R_1$ is methyl, then $R_3$ is haloalkyl, $R_4$ is $NH_2$, $R_1$ is Cl, $R_{13}$ is $CF_3$ and X is N.

Compounds of formula (I) in which $R_1$ is CN will be selected most particularly. Compounds in which $R_2$ is $S(O)_nR_3$, preferably with n=1, $R_3$ preferably being $CF_3$ or alkyl, for example methyl or ethyl, or alternatively n=0, $R_3$ preferably being $CF_3$, as well as those in which X=C—$R_{12}$, $R_{12}$ being a halogen atom, will also be selected. Compounds in which $R_{11}$ is a halogen atom and those in which $R_{13}$ is haloalkyl, preferably $CF_3$, are also preferred. Within the context of the present invention, compounds which combine two or more of these characteristics will advantageously be selected.

A preferred class of compounds of formula (I) consists of compounds such that $R_1$ is CN, $R_3$ is haloalkyl, $R_4$ is $NH_2$, $R_{11}$ and $R_{12}$ are, independently of each other, a halogen atom, and/or $R_{13}$ is haloalkyl. Preferably also, X is C—$R_{12}$.

In these compounds, $R_3$ preferably represents $CF_3$ or ethyl.

In the present invention, the alkyl radicals may contain generally from 1 to 6 carbon atoms. The ring formed by the divalent alkylene radical representing $R_5$ and $R_6$, as well as the nitrogen atom to which $R_5$ and $R_6$ are attached, may be generally a 5-, 6- or 7-membered ring.

A compound of formula (I) which is most particularly preferred in the invention is 1-[2,6-$Cl_2$ 4-$CF_3$phenyl]3-CN 4-[SO—$CF_3$]5—$NH_2$ pyrazole, the common name of which is fipronil.

The two compounds which differ from the above by the following characteristics:

| | |
|---|---|
| 1 - n = 0, | $R_3$ = $CF_3$ |
| 2 - n = 1, | $R_3$ = ethyl | may also be mentioned.

Among the compounds (B), mention may be made in particular of compounds which mimic juvenile hormones, in particular:

azadirachtin-Agridyne diofenolan (Ciba Geigy)

fenoxycarb (Ciba Geigy)

hydroprene (Sandoz)

kinoprene (Sandoz)

methoprene (Sandoz)

pyriproxyfen (Sumitomo/Mgk)

tetrahydroazadirachtin (Agridyne)

4-chloro-2-(2-chloro-2-methylpropyl)-5-(6-iodo-3-pyridylmethoxy)pyridizin-3(2H)-one and chitin-synthesis inhibitors, in particular:

chlorfluazuron (Ishihara Sangyo)

cyromazine (Ciba Geigy)

diflubenzuron (Solvay Duphar)

fluazuron (Ciba Geigy)

flucycloxuron (Solvay Duphar)

flufenoxuron-(Cyanamid)

hexaflumuron (Dow Elanco)

lufenuron (Ciba Geigy)

tebufenozide (Rohm & Haas)

teflubenzuron (Cyanamid)

triflumuron (Bayer)

these compounds being defined by their international common name (The Pesticide Manual, 10th edition, 1994, Ed. Clive Tomlin, Great Britain).

As chitin-synthesis inhibitors, mention may also be made of compounds such as 1-(2,6-difluorobenzoyl)-3-(2-fluoro-4-(trifluoromethyl)phenylurea, 1-(2,6-difluorobenzoyl)-3-(2-fluoro-4-(1,1,2,2-tetrafluoroethoxy)phenylurea and 1-(2,6-difluorobenzoyl)-3-(2-fluoro-4-trifluoromethyl) phenylurea.

Novaluron (Isagro, Italian company) may also be mentioned as a compound (B).

The preferred compounds (B) are methoprenes, pyriproxyfens, hydroprene, cyromazine, lufenuron and 1-(2,6-difluorobenzoyl)-3-(2-fluoro-4-(trifluoromethyl) phenylurea.

Another preferred compound (B) is again nova-luron.

It is preferable for the administration of the two types of compound to be concomitant and preferably simultaneous.

It is preferable for the treatment according to the invention to be carried out every two or, preferably, every three months on cats and dogs.

Preferably, the treatment is carried out so as to administer to the animal a dose of from 0.1 to 40 and in particular from 1 to 20 mg/kg of derivative (A) and a dose of from 0.1 to 40 and in particular 1 to 30 mg/kg of compound (B).

The preferred doses are from 5 to 15 mg/kg for compound (A) and from 0.5 to 15 mg/kg for the preferred compounds (B), or 10 to 20 mg/kg for the other compounds (B).

In another embodiment of the process according to the invention, compounds (A) and (B) may be applied in a distinct and separate manner over time. In this case, it is preferred to alternate the applications with an interval, for example of one month between two applications, the first application preferably being made with compound (A).

It is understood that the dosage values which are thus indicated are average values which may vary within a wide range, since, in practice, a formulation having defined doses of compound (A) of 1-N-phenylpyrazole-type derivative and of compound (B) will be administered to animals having relatively different weights. Consequently, the doses actually applied are often smaller or larger by a factor which may be up to 2, 3 or 4 relative to the preferred dose, without entailing any toxic risk for the animal in the case of an overdose, and while at the same time retaining real efficacy, possibly of shorter duration, in the case of an underdose.

The object of this process is non-therapeutic and relates in particular to the cleaning of animal hairs and skin by elimination of the parasites which are present, as well as their residues and dejections. The treated animals thus have hair which is more pleasant to look at and to feel. This also allows one to avoid the development of fleas in the house.

The invention also relates to such a process for therapeutic purposes, which is intended to treat and prevent parasitoses having pathogenic consequences.

In accordance with the present invention, the process described above may also be used to control ectoparasites, in particular ticks.

The subject of the invention is also a composition, in particular one for controlling fleas on small mammals, characterized in that it includes, on the one hand, at least one compound (A) of formula (I) as defined above, and, on the other hand, at least one compound (B) defined above, in doses and proportions which have parasiticidal efficacy on fleas, in a fluid vehicle which is acceptable for the animal and convenient for local application to the skin, preferably localized over a small surface area.

Preferably, in formula (I);

$R_1$ is CN or methyl $R_2$ is $S(O)_n R_3$ $R_3$ is alkyl or haloalkyl $R_4$ represents a hydrogen or halogen atom; or a radical $NR_5R_6$, $S(O)_m R_7$, $C(O)R_7$, alkyl, haloalkyl or $OR_8$ or a radical —N=C($R_9$)($R_{10}$)

$R_5$ and $R_6$ independently represent a hydrogen atom or an alkyl, haloalkyl, C(O)alkyl or $S(O)_r$—$CF_3$ radical; or $R_5$ and $R_6$ may together form a divalent alkylene radical which may be interrupted by one or two divalent hetero atoms such as oxygen or sulphur $R_7$ represents an alkyl or haloalkyl radical $R_8$ represents an alkyl or haloalkyl radical or a hydrogen atom $R_9$ represents an alkyl radical or a hydrogen atom $R_{10}$ represents a phenyl or heteroaryl group optionally substituted with one or more halogen atoms or groups such as OH, —O-alkyl, S-alkyl, cyano or alkyl $R_{11}$ and $R_{12}$ represent, independently of each other, a hydrogen or halogen atom $R_{13}$ represents a halogen atom or a haloalkyl, haloalkoxy, $S(O)_q CF_3$ or $SF_5$ group m, n, q and r represent, independently of each other, an integer equal to 0, 1 or 2

X represents a trivalent nitrogen atom or a radical C—$R_{12}$, the other three valency positions of the carbon atom forming part of the aromatic ring with the proviso that when $R_1$ is methyl, then $R_3$ is haloalkyl, $R_4$ is $NH_2$, $R_{11}$ is Cl, $R_{13}$ is $CF_3$ and X is N.

Compounds of formula (I) in which $R_1$ is CN will be selected most particularly. Compounds in which $R_2$ is $S(O)_n R_3$, preferably with n=1, $R_3$ preferably being $CF_3$ or alkyl, for example methyl or ethyl, or alternatively n=0, $R_3$ preferably being $CF_3$, as well as those in which X=C—$R_{12}$, $R_{12}$ being a halogen atom, will also be selected. Compounds in which $R_{11}$ is a halogen atom and those in which $R_{13}$ is haloalkyl, preferably $CF_3$, are also preferred. Within the context of the present invention, compounds which combine two or more of these characteristics will advantageously be selected.

A preferred class of compounds of formula (I) consists of compounds such that $R_1$ is CN, $R_3$ is haloalkyl, $R_4$ is $NH_2$, $R_{12}$ and $R_{12}$ are, independently of each other, a halogen atom, and/or $R_{13}$ is haloalkyl.

In these compounds, $R_3$ preferably represents $CF_3$ or ethyl.

A compound of formula (I) which is most particularly preferred in the invention is 1-[2,6-$Cl_2$ 4-$CF_3$phenyl]3-CN 4-[SO—$CF_3$] 5-$NH_2$ pyrazole.

The two compounds which differ from the above by the following characteristics:

| | |
|---|---|
| 1 – n = 0, | $R_3 = CF_3$ |
| 2 – n = 1, | $R_3$ = ethyl | may also be mentioned.

The compounds of formula (I) may be prepared according to one or other of the processes described in patent applications WO-A-87/3781, 93/6089, 94/21606 or European patent application EP-A-0,295,117, or any other process which falls within the competence of a specialist skilled in the art of chemical synthesis. For the chemical preparation of the products of the invention, a person skilled in the art is considered as having at his disposal, inter alia, all of the contents of "Chemical Abstracts" and the documents cited therein.

Among the compounds of IGR type listed above, methoprenes, pyriproxyfens, hydroprene, cyromazine, lufenuron and 1-(2, 6-difluorobenzoyl)-3-(2-fluoro-4-(trifluoromethyl)phenylurea are preferred.

Novaluron is also preferred.

The proportions, by weight, of compounds of formula (I) and of compound (B) are preferably between 80/20 and 20/80.

The fluid vehicle may be simple or complex and it is adapted to the route and mode of administration selected.

The compositions for spot-on application can advantageously comprise:

b) a crystallization inhibitor, in particular one which is present in a proportion of from 1 to 20% (W/V), preferably from 5 to 15%, this inhibitor satisfying the test according to which:

0.3 ml of a solution A comprising 10% (W/V) of the compound of formula (I) in the solvent defined in c) below, along with 10% of this inhibitor, are deposited on a glass slide at 20° C. for 24 hours, after which it is observed with the naked eye that there are few or no crystals, in particular fewer than 10 crystals, preferably 0 crystals on the glass slide, c) an organic solvent having a dielectric constant of between 10 and 35, preferably of between 20 and 30, the content of this solvent c) in the overall composition preferably representing the difference to make the composition up to 100%, d) an organic cosolvent having a boiling point of below 100° C., preferably of below 80° C., and having a dielectric constant of between 10 and 40, preferably of between 20 and 30; this cosolvent may advantageously be present in the composition in a d)/c) weight/weight (W/W) ratio of between 1/15 and 1/2. The solvent is volatile, so as to serve in particular as a drying promoter, and is miscible with water and/or with the solvent c).

Although this is not preferred, the composition for spot-on application may optionally comprise water, in particular in a proportion of from 0 to 30% (volume per unit volume, V/V), in particular from 0 to 5%.

The composition for spot-on application may also comprise an antioxidant intended to inhibit air-oxidation, this agent being present in particular in a proportion of from 0.005 to 1% (W/V), preferably from 0.01 to 0.05%.

The compositions according to the invention intended for pets, in particular cats and dogs, are generally applied by being deposited onto the skin ("spot-on" or "pour-on" application); this is generally a localized application over a surface area of less than 10 cm$^2$, especially of between 5 and 10 cm$^2$, in particular at two points and preferably localized between the animal's shoulders. Once deposited, the composition diffuses, in particular over the animal's entire body, and then dries without crystallizing or modifying the appearance (in particular absence of any whitish deposit or dusty appearance) or the feel of the fur.

The compositions for spot-on application according to the invention are particularly advantageous owing to their efficacy, their speed of action and the pleasant appearance of the animal's fur after application and drying.

As organic solvent c) which can be used in the invention, mention may be made in particular of: acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, in particular N-methylpyrrolidone, diethylene glycol monoethyl ether, ethylene glycol and diethyl phthalate, or a mixture of at least two of these solvents.

As crystallization inhibitor b) which can be used in the invention, mention may be made in particular of:

polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, acrylic derivatives such as methacrylates and the like, anionic surfactants such as alkaline stearates, in particular sodium, potassium or ammonium stearate; calcium stearate; triethanolamine stearate; sodium abietate; alkyl sulphates, in particular sodium lauryl sulphate and sodium cetyl sulphate; sodium dodecylbenzenesulphonate, sodium dioctylsulphosuccinate; fatty acids, in particular those derived from coconut oil, cationic surfactants such as water-soluble quaternary ammonium salts of formula N$^+$R'R"R'"R"",Y$^-$ in which the radicals R are optionally hydroxylated hydrocarbon radicals and Y$^-$ is an anion of a strong acid such as the halide, sulphate and sulphonate anions; cetyltrimethylammonium bromide is among the cationic surfactants which can be used, amine salts of formula N$^+$R'R"R'" in which the radicals R are optionally hydroxylated hydrocarbon radicals; octadecylamine hydrochloride is among the cationic surfactants which can be used, nonionic surfactants such as optionally polyoxyethylenated sorbitan esters, in particular polysorbate 80, polyoxyethylenated alkyl ethers; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, amphoteric surfactants such as substituted lauryl compounds of betaine, or preferably a mixture of at least two of these crystallization inhibitors.

In a particularly preferred manner, a crystallization inhibitor couple, namely the combination of a film-forming agent of polymeric type and a surfactant, will be used. These agents will be chosen in particular from the compounds mentioned as crystallization inhibitor b).

Among the film-forming agents of polymeric type which are particularly advantageous, mention may be made of:

the various grades of polyvinylpyrrolidone, polyvinyl alcohols, and copolymers of vinyl acetate and vinylpyrrolidone.

As regards the surfactants, mention will be made most particularly of nonionic surfactants, preferably polyoxyethylenated sorbitan esters and in particular the various grades of polysorbate, for example polysorbate 80.

The film-forming agent and the surfactant may be incorporated, in particular, in similar or identical amounts within the limit of the total amounts of crystallization inhibitor mentioned elsewhere.

The couple thus produced ensures the objectives of absence of crystallization on the hairs and maintenance of the cosmetic appearance of the coat in a note-worthy manner, that is to say without any tendency towards stickiness or to a sticky appearance, despite the high concentration of active material.

As cosolvent d), mention may be made in particular of: absolute ethanol, isopropanol, methanol.

As antioxidant, standard agents are used in particular, such as: butylhydroxyanisole, butylhydroxytoluene, ascorbic acid, sodium metabisulphite, propyl gallate and sodium thiosulphate, or a mixture of not more than two of these agents.

The compositions for spot-on application according to the invention are usually prepared by simple mixing of the constituents as defined earlier; advantageously, to begin with, the active material is mixed in the main solvent and the other ingredients or adjuvants are then added.

The volume applied may be from about 0.3 to 1 ml, preferably about 0.5 ml for cats, and from about 0.3 to 3 ml for dogs, according to the weight of the animal.

In a particularly preferred manner, the composition according to the invention may be in the form of a concentrated emulsion, suspension or solution for spot-on application to a small area of the animal's skin, generally between the two shoulders (spot-on type solution). In a clearly less preferred manner, forms of solution or suspension to be sprayed, forms of solution, suspension or emulsion to be poured or spread onto the animal (pour-on type solution) an oil, a cream, an ointment or any other fluid formulation for topical administration may be provided.

Advantageously, the ready-to-use composition contains a dose of from 0.1 to 40 mg/kg of compound (A) of formula (I) and 0.1 to 40 mg/kg of compound (B).

Preferably, a ready-to-use dosed formulation, in particular one for spot-on application, contains 1 to 20 mg/kg, preferably 2 to 10 mg/kg of compound (A), in particular fipronil, and from 1 to 30 mg/kg, preferably 2 to 10 mg/kg, of preferred compound (B) or 10 to 20 mg/kg of other compound (B).

Advantageously, ready-to-use compositions dosed for 1–10, 10–20 and 20–40 kg animals respectively may be provided.

In another embodiment, provided for separate application over time, a composition may be made in the form of a kit separately combining, in the same packaging, a composition containing a compound of formula (I), in particular fipronil, and a composition containing compound (B), preferably pyriproxyfen, each of the compositions including a vehicle which allows it to be applied onto the skin.

Preferably, each of the two compositions is provided for local spot-on application and, preferably, a container containing just the dose required is provided for each application.

Thus, for example, a kit may contain, in a package, three containers each containing a single dose of composition of compound (A) and three containers each containing a single dose of composition of compound (B), the containers (A) being distinguished from the containers (B) by markings, shapes or colours, as well as a notice specifying that the containers (A) and (B) must be used alternately with an interval, for example, of one month, and starting, for example, with a container (A).

The compositions according to the invention, in particular those for spot-on application, have proven to be extremely effective for the very long-lasting treatment of fleas on mammals, and in particular small mammals such as cats and dogs.

The discovery that the compound (A), such as fipronil, dissolves in the sebum so as to cover the entire animal and becomes concentrated in the sebaceous glands, from which it is gradually released over a very long period, is a plausible explanation of this long-lasting efficacy for these compositions, and could perhaps also explain the long-lasting action of the associated compound (B).

They also have a certain efficacy against other parasitic insects and, in particular, ticks, and it is understood that the application of the composition according to the invention may be extended to the treatment of ectoparasites, or even endoparasites for which the composition proves to have real utility capable of being obtained practically, according to the criteria of the veterinary art.

Thus, for example, a composition based on fipronil and fluazuron may also be used in particular against ticks.

Where appropriate, the composition according to the invention may also comprise another insecticide, and in particular imidaclopride.

The subject of the invention is also the use of at least one compound (A) of formula (I) and of at least one compound (B) of IGR type, as defined above, for the preparation of a composition as defined above.

Other advantages and characteristics of the invention will become apparent on reading the description which follows, which is given by way of non-limiting example.

The composition preparation example which follows includes, as compound (A) of formula (I), the compound known as fipronil.

By way of example to prepare a composition for local application to the skin according to the invention, the following components may advantageously be mixed together:

a1—compound (B) in a proportion of from 1 to 20% (percentage as a weight per unit volume W/V)

a2—compound (A) of formula (I), in a proportion of from 1 to 20%, preferably 5 to 15% (percentage as a weight per unit volume W/V).

By way of example, the compositions according to the invention comprise the following concentrations (W/V) of compounds (A) and (B) in a liquid medium comprising a representative of each of the components b, c and d. The total volume is 1 ml.

EXAMPLE 1 fipronil 10%
pyriproxyfen 5%

EXAMPLE 2 fipronil 5%
pyriproxyfen 5%

EXAMPLE 3 fipronil 5%
pyriproxyfen 20%

EXAMPLE 4 fipronil 10%
methoprene 30%

EXAMPLE 5 fipronil 10%
1-(2,6-difluorobenzoyl)-3-(2-fluoro-4-trifluoromethyl) phenylurea 5%.

Cats are infested with 100 fleas each, and are then reinfested every 10 days. Concomitant with the first manifestation, they receive a local skin application of 0.1 ml/kg of the composition according to Example 1. Two months after the treatment and ten days after the last infestation, no fleas are detected and the eggs collected are found to be non-viable.

Dogs treated according to the same procedure with compositions according to Examples 1 and 2 show the same efficacy of treatment two months after application of the composition.

What is claimed is:

1. A synergistic spot-on composition for the long lasting protection against ectoparasites on mammals which comprises synergistic amounts (A) at least one compound of the formula:

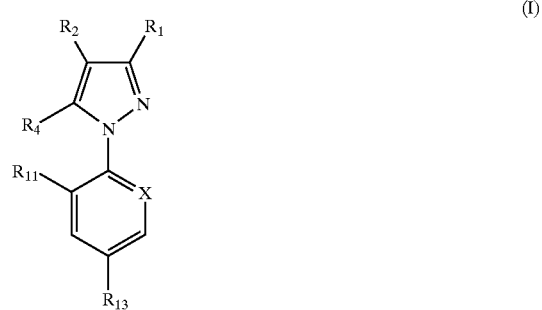

in which:

$R_1$ is CN or methyl or a halogen atom;

$R_2$ is $S(O)_n R_3$ or 4,5-dicyanoimidazol-2-yl or haloalkyl;

$R_3$ is alkyl or haloalkyl;

$R_4$ represents a hydrogen or halogen atom; or a radical $NR_5R_6$, $S(O)_m R_7$, $C(O)R_7$, $C(O)O—R_7$, alkyl, haloalkyl, or $OR_8$ or a radical $—N=C(R_9)(R_{10})$;

$R_5$ and $R_6$ independently represent a hydrogen atom or an alkyl, haloalkyl, C(O)alkyl, alkoxycarbonyl or $S(O)_r$—$CF_3$ radical; $R_5$ and $R_6$ may together form a divalent alkylene radical which may be interrupted by one or two divalent hereto atoms or;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl group optionally substituted with one or more halogen atoms or one or more substituents selected from the group consisting of OH, —O-alkyl, S-alkyl, cyano or alkyl;

$R_{11}$ and $R_{12}$ represent, independently of each other, hydrogen, halogen, CN or $NO_2$;

$R_{13}$ represents a halogen atom or a haloalkyl, haloalkoxy, $S(O)_qCF_3$ or $SF_5$ group;

m, n, q and r represent, independently of each other, an integer equal to 0, 1 or 2;

X represents a trivalent nitrogen atom or a radical C—$R_{12}$, the other three valency positions of the carbon atom forming part of the aromatic ring;

with the proviso that when $R_1$ is methyl, then $R_3$ is haloalkyl, $R_4$ is $NH_2$, $R_{11}$ is Cl, $R_{13}$ is $CF_3$ and X is N; or $R_2$ is 4,5-dicyanoimidazol-2-yl, $R_4$ is Cl, $R_{11}$ is Cl, $R_{13}$ is $CF_3$ and X is =C—Cl;

(B) at least one insect growth regulator (IGR) that mimics juvinile hormones;

(C) imidacloprid; and a fluid vehicle comprising at least one customary spot-on formulation adjuvant.

2. The synergistic spot-on composition according to claim 1, which comprises a compound of formula (I) wherein:

$R_1$ is CN or methyl;

$R_2$ is $S(O)_nR_3$;

$R_3$ is alkyl or haloalkyl;

$R_4$ represents a hydrogen or halogen atom; or a radical $NR_5R_6$, $S(O)_mR_7$, $C(O)R_7$, alkyl, haloalkyl or $OR_8$ or a radical —N=C($R_9$) ($R_{10}$);

$R_5$ and $R_6$ independently represent a hydrogen atom or an alkyl, haloalkyl, C(O)alkyl or $S(O)_r$-$CF_3$ radical; or $R_5$ and $R_6$ may together form a divalent alkylene radical which may be interrupted by one or two divalent hetero atoms selected from the group consisting of oxygen and sulphur;

$R_7$ represents an alkyl or haloalkyl radical;

$R_8$ represents an alkyl or haloalkyl radical or a hydrogen atom;

$R_9$ represents an alkyl radical or a hydrogen atom;

$R_{10}$ represents a phenyl or heteroaryl group optionally substituted with one or more halogen atoms or one or more substituents selected from the group consisting of OH, —O-alkyl, S-alkyl, cyano or alkyl;

$R_{11}$ and $R_{12}$ represent, independently of each other, a hydrogen or halogen atom;

$R_{13}$ represents a halogen atom or a haloalkyl, haloalkoxy, $S(O)_qCF_3$ or $SF_5$ group;

m, n, q and r represent, independently of each other, an integer equal to 0, 1 or 2;

X represents a trivalent nitrogen atom or a radical C—$R_{12}$, the other three valency positions of the carbon atom forming part of the aromatic ring;

with the proviso that when $R_1$ is methyl, then $R_3$ is haloalkyl, $R_4$ is $NH_2$, $R_{11}$ is Cl, $R_{13}$ is $CF_3$ and X is N;

(D) a fluid vehicle.

3. The synergistic spot-on composition according to claim 1, which comprises a compound of formula (I) wherein $R_1$ is CN.

4. The synergistic spot-on composition according to claim which comprises a compound of formula (I) wherein $R_{13}$ is haloalkyl.

5. The synergistic spot-on composition according to claim 1, which comprises a compound of formula (I) wherein $R_2$ is $S(O)_nR_3$, where when n=1, $R_3$ is $CF_3$ or alkyl, or where n=0, $R_3$ is $CF_3$.

6. The synergistic spot-on composition according to claim 1, which comprises a compound of formula (I) where X is C—$R_{12}$ where $R_{12}$ is a halogen atom.

7. The synergistic spot-on composition according to claim 1, which comprises a compound of formula (I) where $R_1$ is CN, $R_3$ is haloalkyl, $R_4$ is $NH_2$, $R_{11}$ and $R_{12}$ are, independently of each other, a halogen atom, and/or $R_{13}$ is haloalkyl.

8. The syngergistic spot-on composition according to claim 1, in which the compound of formula (I) 1-[2,6-$Cl_2$4-$CF_3$ phenyl]3-CN4-[SO—$CF_3$]5-$NH_2$ pyrazole.

9. The synergistic spot-on composition according to claim 1, in which the compound of formula (I) is compounds 1-[2,6-$Cl_2$4-$CF_3$ phenyl]3-CN4-[S—$CF_3$]5-$NH_2$ pyrazole or 1-[2,6-$Cl_2$4-$CF_3$ phenyl]3-CN 4-[SO—$C_2H_5$]5-$NH_2$ pyrazole.

10. The synergistic spot-on composition according to claim 1, wherein the compound which mimics juvenile hormones is selected from the group consisting of:

azadirachtin, diofenolan, fenoxycarb, hydroprene, kinoprene, methoprene, pyriproxyfen, tetrahydroazadrirachtin, and 4-chloro-2-(2-chloro-2-methyl-propyl)-5-(6-iodo-3-pyridylmethoxy) pyridizine-3(2H)-one.

11. The synergistic spot-on composition according to claim 1, wherein IGR is methoprene.

12. The synergistic spot-on composition according to claim 1, wherein in that the proportions, by weight, of compounds (A) to the compounds (B) are between 80/20 and 20/80.

13. The synergistic spot-on composition according to claim 1, wherein the fluid vehicle and the concentration of the compounds (A) and (B) are applied locally on a zone with a surface area of less then 10 $cm^2$.

14. The synergistic spot-on composition according to claim 1, wherein amount of compound (A) is from 0.1 to 40 mg/kg and the amount of compound (B) is from 0.1 to 40 mg/kg.

15. The synergistic spot-on composition according to claim 14, wherein the amount of compound (A) is from 1 to 20 mg/kg, and the amount of compound (B) is from 1 to 30 mg/kg.

16. The synergistic spot-on composition according to claim 1, which further comprises a crystallization inhibitor which is present in a proportion of from 1 to 20% (W/V).

17. The synergistic spot-on composition according to claim 16, wherein the crystallization inhibitor is selected from the group consisting of:

polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters, lecithin, sodium carboxymethylcellulose, acrylic derivatives, at least one anionic surfactants, at least one cationic surfactant, at least one amine salt of the formula $N^{30}$ R'R"R'" in which the radicals R are optionally hydroxylated hydrocarbon radicals;

at least one non-ionic surfactant, at least one amphoteric surfactant, and a mixture of at least two of these crystallization inhibitors.

18. The synergistic spot-on composition according to claim 17, wherein:

the anionic surfactants is alkaline stearate, calcium stearate; triethanolamine stearate; sodium abietate; alkyl sulphates, sodium dodecylbenzenesulphonate, sodium dioctylsulphosuccinate; and fatty acids;

the cationic surfactant is a water-soluble quaternary ammonium salts of formula N⁺R'R"R'''R"", Y⁻ in which the radicals R are optionally hydroxylated hydrocarbon radicals and Y⁻ is an anion of a strong acid;

the amine salt octadecylamine hydrochloride;

the nonionic surfactant is polysorbate 80, polyoxyethylenated alkyl ethers; polyethylene glycol stearate, polyoxyethylenate derivatives of castor oil, polyglycerol esters, polyoxyethylenate fatty alcohols polyoxyethylenate fatty acids, copolymers of ethylene oxide and propylene oxide;

the amphoteric surfactant is a substituted lauryl compounds of betaine.

19. The synergistic spot-on composition according to claim 17, wherein the crystallization inhibitor is a crystallization inhibitor couple formed by the combination of a film-forming agent of polymeric type and a surfactant.

20. The synergistic spot-on composition according to claim 19, wherein the film-forming agent is polyvinylpyrrolidone, polyvinyl alcohols, or copolymers of vinyl acetate and vinyl pyrrolidone, and the surfactant is an ionic surfactants.

21. The synergistic spot-on composition according to claim 1, wherein the fluid vehicle comprises an organic solvent having a dielectric constant of between 10 and 35.

22. The synergistic spot-on composition according to claim 21, wherein the organic solvent is selected from the group consisting of acetone, acetonitrile, benzyl alcohol, butyldiglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, diethylene glycol monoethyl ether, ethylene glycol, diethyl phthalate, and a mixture of at least two of these solvents.

23. The synergistic spot-on composition according to claim 21, wherein the fluid vehicle further comprises an organic co-solvent having a boiling point below 100° C., a dielectric constant of between 10 and 40, and is miscible with water and/or with the solvent and present in a weight ratio of co-solvent:solvent between 1:15 and 1:2.

24. The synergistic spot-on composition according to claim 23, wherein the co-solvent is absolute ethanol, isopropanol or methanol.

25. A kit comprising, separately in the same packaging, at least one container containing an effective amount of a compound (A) according to claim 1 and at least one fluid vehicle, at least one container containing an effective amount of a compound (B) according to claim 1 and at least one fluid vehicle, and at least one container containing an effective amount of imidacloprid and at least one fluid vehicle, and a notice specifying that the containers are to be used alternatively with an interval.

26. The synergistic spot-on composition according to claim 1, characterized in that it affords protection for 2 to 3 months.

27. A method for controlling ectoparasites in mammals over a long duration of time which comprises applying locally to the skin of a mammal a synergistically effective amount of a synergistic spot-on composition according to claim 1.

28. The method according to claim 27, wherein the mammal is a cat or dog.

29. The method according to claim 27, wherein the proportions, by weight, of compounds (A) to compounds (B) are between 80/20 and 20/80.

30. The method according to claim 27, wherein the synergistic spot-on composition comprises from 0.1 to 40 mg/kg of compound (A) and from 0.1 to 40 mg/kg of compound (B).

31. The method according to claim 27, wherein the synergistic spot-on composition comprises from 1 to 20 mg/kg and from 1 to 30 mg/kg of compound (B).

32. The method according to claim 27, wherein the ectoparasite is a flea or tick.

33. The method according to claim 28, wherein the synergistic spot-on composition comprise from 2 to 10 mg/kg of compound (B).

34. The method according to claim 27, wherein the duration is two months.

35. The method according to claim 27, wherein the duration is three months.

36. The method according to claim 27, wherein the synergistic spot-on composition comprises of fipronil, methoprene and imidacloprid.

* * * * *